Figure 1:
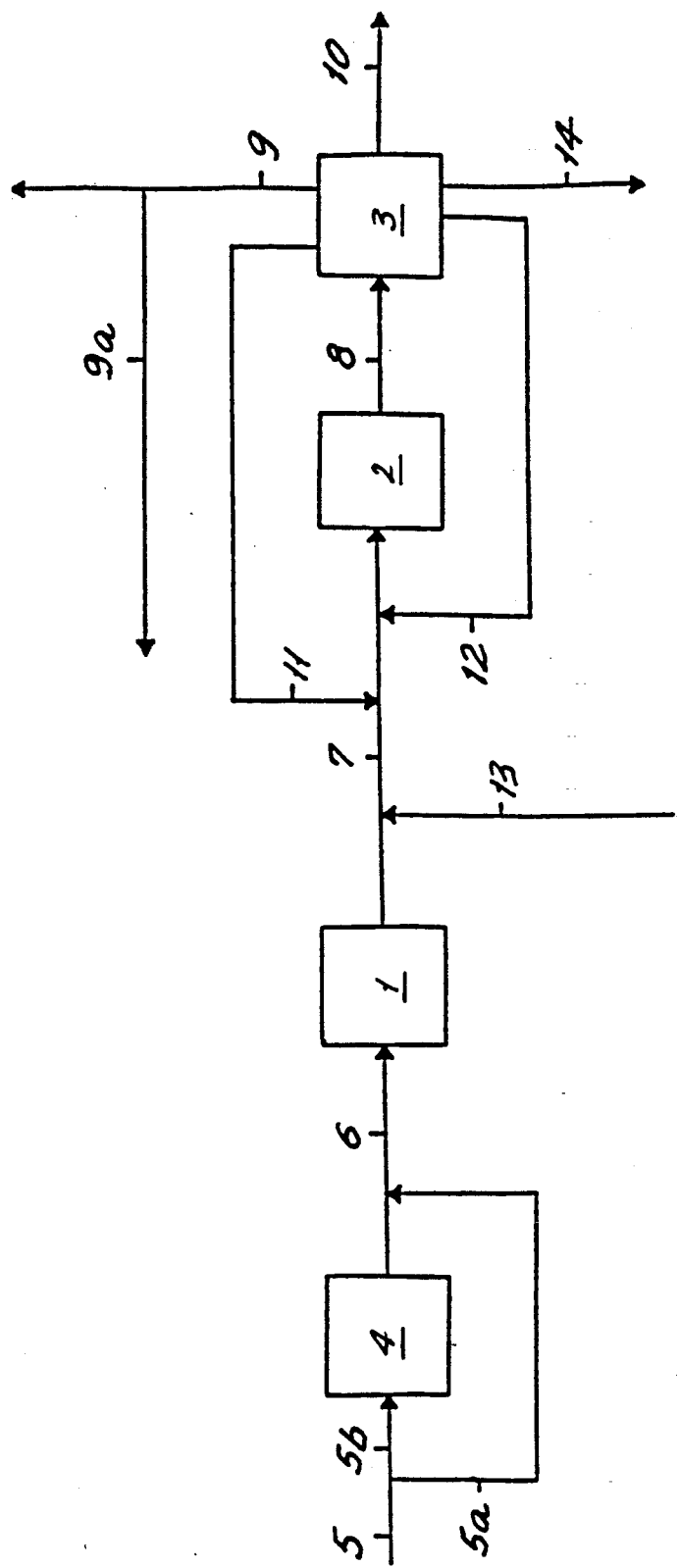

United States Patent [19]

Hansen et al.

[11] Patent Number: 5,189,203

[45] Date of Patent: Feb. 23, 1993

[54] PROCESS FOR PREPARING ACETIC ACID, METHYL ACETATE, ACETIC ANHYDRIDE OR MIXTURES THEREOF

[75] Inventors: John B. Hansen, Helsingor; Finn H. Joensen, Horsholm; Haldor F. A. Topsoe, Vedbaek, all, Denmark

[73] Assignee: Haldor Topsoe A/S, Denmark

[21] Appl. No.: 213,584

[22] Filed: Jun. 30, 1988

[30] Foreign Application Priority Data

Jun. 30, 1987 [DK] Denmark ............... 3348/87

[51] Int. Cl.$^5$ ............... C07C 67/36; C07C 51/10; C07C 51/12; C07C 51/14
[52] U.S. Cl. ............... 560/232; 562/517; 562/519; 562/890; 562/891
[58] Field of Search ............... 560/232; 562/517, 519, 562/890, 891

[56] References Cited

U.S. PATENT DOCUMENTS

| | | |
|---|---|---|
| 3,689,533 | 9/1972 | Schultz ............... 560/232 |
| 3,816,513 | 6/1974 | Wakamatsu et al. ............... 560/232 |
| 4,356,320 | 10/1982 | Naglieri et al. ............... 562/519 |
| 4,430,273 | 2/1984 | Erpenbach et al. ............... 562/891 |

FOREIGN PATENT DOCUMENTS

| | | |
|---|---|---|
| 162263 | 11/1985 | European Pat. Off. ............ 562/607 |
| 2610036 | 9/1972 | Fed. Rep. of Germany. |
| 39-25031 | 11/1964 | Japan ............... 560/232 |

Primary Examiner—Jose G. Dees
Assistant Examiner—Joseph M. Conrad, III
Attorney, Agent, or Firm—Ostrolenk, Faber, Gerb & Soffen

[57] ABSTRACT

The present invention relates to a process for preparing acetic acid, acetic acid methyl ester or acetic anhydride or mixtures thereof by converting a synthesis gas mainly containing hydrogen and carbon oxides, by first converting the synthesis gas catalytically into a gas mixture containing methanol and dimethyl ether and then carbonylating this mixture catalytically into acetic acid and/or methyl acetate and/or acetic anhydride.

6 Claims, 1 Drawing Sheet

PROCESS FOR PREPARING ACETIC ACID, METHYL ACETATE, ACETIC ANHYDRIDE OR MIXTURES THEREOF

DESCRIPTION OF THE PRIOR ART

It is well-known to convert a synthesis gas mixture as mentioned catalytically into methanol according to the reaction $$CO + 2H_2 \rightleftharpoons CH_3OH \tag{1}$$

Examples of suitable methanol synthesis catalysts are oxides of zinc and chromium; oxides of zinc, copper and chromium; and oxides of zinc, copper and aluminium; as well as zinc-copper-chromium-lanthanum oxides. Under typical conditions of reaction these catalysts will also catalyze the water gas reaction (shift reaction)

$$CO + H_2O \rightleftharpoons CO_2 + H_2 \tag{3}$$

In conventional methanol synthesis, which typically takes place at 220°–400° C. and 10–500 kg/cm², the degree of conversion per passage is usually low because of an unfavourable equilibrium of methanol formation in reaction (1), and for this reason high ratios of recycling are needed, usually from 4:1 to 10:1. In order to improve the equilibrium it has been proposed (in connection with the conversion of synthesis gas into petrol (gasoline)) in U.S. patent specification No. 3,894,102 to combine the methanol synthesis with the catalytical conversion of a substantial proportion of the methanol formed into dimethyl ether according to the methanol dehydration reaction $$2\ CH_3OH \rightleftharpoons CH_3OCH_3 + H_2O \tag{2}$$

Many materials are known to catalyze this reaction, notably the socalled acidic dehydration catalysts as for instance γ-alumina (which is employed according to the above patent specification), silica, silica-alumina and crystalline aluminosilicates such as zeolites.

Reactions (1) to (3) are normally carried out heterogenically in gas phase over a solid, optionally supported catalyst.

It is well-known to carbonylate alkanols and ethers catalytically into carboxylic acids containing one carbon atom more than the starting material, and esters or anhydrides thereof, specifically to carbonylate methanol and dimethyl ether to form acetic acid, its anhydride or methyl acetate according to the reactions $$CH_3OH + CO \rightarrow CH_3COOH \tag{4}$$

$$CH_3OCH_3 + CO \rightarrow CH_3COOCH_3 \tag{5}$$

$$CH_3OCH_3 + 2CO \rightarrow (CH_3CO)_2O \tag{6}$$

and $$CH_3COOCH_3 + CO \rightarrow (CH_3CO)_2O \tag{7}$$

These reactions have been carried out in liquid phase and in gas phase over a solid catalyst bed, and various catalysts have been proposed, especially noble metal catalyst. A few publications on these reactions are mentioned in the following.

In U.S. Pat. No. 3,689,533 there is mentioned a number of drawbacks in older carbonylation reactions (4) and (5), notably a low degree of conversion and many by-products, in part difficult to remove. To overcome these drawbacks this patent proposes to react methanol and dimethyl ether with carbon monoxide in gas phase at a temperature of 50°–500° C. and a CO partial pressure of 0.07 to 1050 kg/cm² abs., preferably 0.7–50 kg/cm² abs, in the presence of a supported rhodium catalyst promoted with iodine, bromine or compounds thereof. It appears from the specification that CO is added in a pure form but in certain cases steam may be present.

The slightly older British patent specification No. 1,233,121 enumerates the same drawbacks in known carbonylation reaction as the above US patent specification and proposes a similar reaction as that, but conducted in liquid phase (homogenous catalysis), viz. the carbonylation of an alkyl compound containing n carbon atoms (n being an integer 6–20) in the form of an alcohol, a halide, an ester or an ether by the reaction at a temperature of at least 50° C. with carbon monoxide in the presence of a catalyst of rhodium or a rhodium compound and a promoter selected amongst bromine, iodine and compounds thereof. In Ullmann's Encyclopedia of Industrial Chemistry, 5th edition, vol. A1, page 47, VCH Verlagsgesellschaft, Weinheim, it is stated that this process, which is known as the Monsanto process when the alkyl compound is methanol and which has gained industrial spreading, leads to the carbonylation of methanol into acetic acid in a yield of 99%, calculated from methanol, and 90%, calculated from CO. Important by-products are stated to be hydrogen and carbon dioxide formed via the water gas shift reaction (3), which is known to be catalyzed by rhodium under homogenous process conditions (Ullmann, l.c. p. 49 and J. Am. Chem. Soc. 99, 2791, 1977), accompanied by a significant loss of valuable CO. In this process methanol is also added in pure form. The methanol process suffers, as mentioned, from unfavourable equilibria, which apart from a high reaction pressure call for cooling of the entire process stream, condensation of methanol and recycling of remaining large amounts of unconverted synthesis gas.

It is moreover known from U.S. patent specification No. 4,356,320 to conduct the carbonylation by the aid of a base metal catalyst, viz. a nickel catalyst in the presence of an organophosphorus(III) compound and using an iodide. Even in this case CO and methanol are added in pure form.

It is characteristic for the carbonylation processes mentioned that the carbonylation reaction is of the order zero with respect to carbon monoxide as well as methanol and dimethyl ether. As moreover the reactions (4)–(7) have equilibrium almost completely in favour of the products, one is free to choose space velocity, pressure and temperature in a way so as to obtain close to complete conversion of the reactants in one single passage through the reactor.

From German patent specification No. 26 10 036 there is known a process for preparing symmetric or unsymmetric carboxylic anhydrides of the formula $(RCO)_2O$, wherein R denotes $C_{1-4}$ alkyl and hence specifically acetic anhydride, from the corresponding alkyl alkanoates or alkyl ethers, i.e. specifically according to reactions (6) and (7), under substantially anhydrous conditions in the presence of noble metal catalysts of group VIII of the Periodical Table of Elements, and a complex promoter containing at least an organonitrogen or organophosphorus compound where N and P are trivalent, together with a metal belonging to groups IVa, Va or VIa of the Periodical Table of Elements; the reaction takes place at a CO partial pressure of 0.07–678 bar and a temperature of 25°–350° C. The specification mentions that carbonylation at low pressures earlier had only resulted in acetic acid, whereas carbonylation in acetic anhydride only could be carried out a very elevated pressures, a disadvantage which is told to have been remedied by using the abovementioned catalyst system. The reaction is normally carried out at moderately elevated pressure, e.g. 1–69 and preferably 2–14 bar, and the reaction time is in the range of 0.1–20 hours dependent of the temperature and pressure. It is advantageously conducted in liquid phase (homogeneously) with a solvent or diluent present. As noble metal catalyst there is preferably employed a rhodium compound.

German published patent specification No. 34 40 646 describes the preparation of monocarboxylic anhydrides ($RCO)_2O$ by the reaction of the corresponding alkyl alkanoates or alkyl ethers in gas phase by gas phase catalysis with a supported catalyst with an organosilicon compound having alkoxy or halogen groups as well as organonitrogen, organophosphorus, organoarsenic, organosulphur, mercapto or thioether groups as a polyfunctional attachment agent between the support at one hand and a noble metal compound of group VIII in the Periodical Table of Elements at the other hand. The specification says that there is obtained an improved catalyst activity and selectivity compared to the use of supports impregnated with catalyst solutions.

The fundamental reactions in the conversion according to the invention thus are well-known per se but it has not been suggested to combine them in one reaction sequence as here proposed. However, it has now been surprisingly found that there is obtained a technically simple reaction sequence and a high degree of conversion, based on the synthesis gas, by such a combination.

DESCRIPTION OF THE INVENTION

As explained, in the known processes for carbonylation of methanol and dimethyl ether to acetic acid and methyl acetate or the anhydride, the needful carbon monoxide has been added as such. In practice carbon monoxide is normally obtained by various reactions which involve the reforming of methane or higher hydrocarbons. In the synthesis gas thereby formed, CO is present along with $H_2$ and $CO_2$ which accordingly have to be separated, e.g. by an expensive cryoseparation, in order to provide the feed gas needed. It is a particular advantage in the present process that one avoids this separation, avoids a separate preparation of methanol and in a coherent reaction sequence by a suitable control of the reactions and recycling streams can obtain a high degree of conversion of a synthesis gas as stated into acetic acid, methyl acetate, acetic anhydride or mixtures thereof.

This is obtained if according to the invention one combines the two set of reactions initially stated by (i) adjusting the synthesis gas to form a feed gas which, optionally after the removal of some carbon dioxide, contains CO and $CO_2$ in a mol ratio of 0.5:1 to 20:1 and passing this feed gas to a first reactor in which at a pressure of 5–200 bar and a temperature of 150°–400° C. it is heterogenically (in gas phase) converted into methanol in the presence of one or more catalysts that together catalyze the reactions $$CO + 2 H_2 \rightleftharpoons CH_3OH \tag{1}$$

$$2 CH_3OH \rightleftharpoons CH_3OCH_3 + H_2O \tag{2}$$

and $$CO + H_2O \rightleftharpoons CO_2 + H_2 \tag{3}$$

at least a substantial proportion of the methanol formed being converted into dimethyl ether in the same reactor, the reaction parameters being controlled in a manner so as to obtain a mol proportion $Re = 0.1:1$ to $3:1$ of carbon monoxide to methanol plus dimethyl ether, defined by the equation $Re = CO/(CH_3OH + 2CH_3OCH_3)$, subsequently (ii) passing the entire effluent, after having optionally added $H_2O$ in an amount so as to cause the effluent to contain $H_2O$ and dimethyl ether in a mol proportion of zero to about 1, from the first reactor to a second reactor in which methanol and dimethyl ether are converted into the desired acetic acid product in gas phase or liquid phase, at a pressure of 1–800 bar and a temperature of 100°–500° C., in the presence of one or more catalysts which together catalyze the carbonylating reactions, $$CH_3OH + CO \rightarrow CH_3COOH \tag{4}$$

$$CH_3OCH_3 + CO \rightarrow CH_3COOCH_3 \tag{5}$$

and optionally also $$CH_3OCH_3 + 2CO \rightarrow (CH_3CO)_2O \tag{6}$$

and $$CH_3COOCH_3 + CO \rightarrow (CH_3CO)_2O \tag{7}$$

as well as optionally even the hydrolysis $$CH_3COOCH_3 + H_2O \rightleftharpoons CH_3COOH + CH_3OH \tag{8}$$

and if desired the water gas shift reaction (3) to provide a sufficient amount of carbon monoxide to complete the conversion of methanol and dimethyl ether to the desired acetic acid product if the mol proportion is substantially below that stoichiometrically needed therefor, and then (iii) obtaining from the effluent from the second reactor at least one product stream consisting of an acetic acid product as defined above, at least one or more exit streams and recycle streams being separated off.

The catalysts in the first reactor may be intimately mixed in a single bed or in a series of alternate beds, or the methanol synthesis catalyst (which as mentioned is also active in the water gas shift reaction) may be deposited on a support which is active as catalyst in the methanol dehydration reaction.

As catalyst system in step (i) there is particularly expediently according to the invention used a mixture of $CuO-ZnO-Al_2O_3$ having a composition of about 60 atom % Cu, 25 atom % Zn and 15 atom % Zn, as well as zeolites rich in silicon, e.g. of the type HZSM-5.

If the catalyst system chosen in step (ii) is not active in the water gas shift reaction (3), it is important to choose the reaction parameters in step (i) in such a way that the mol ratio Re of carbon monoxide at one hand and methanol and dimethyl ether at the other hand, hand, defined by the equation $$Re = CO/(CH_3OH + 2CH_3OCH_3)$$

is approximately stoichiometric with respect to the product or products formed in step (ii), i.e. about 0.5 if methyl acetate is desired and about 1 if acetic acid or its anhydride is desired. If a product mixture is desired, e.g. of methyl acetate or acetic anhydride, R may assume values between 0.5 and 1. After the reactions in step (i) there should in all cases be the sufficient amount of carbon monoxide present for use in step (ii). The effluent from step (i) may be close to an equilibrium shifted to the right with respect to the water gas reaction (3) and typically contains substantial amounts of unreacted hydrogen and carbon dioxide which both act as inert gases in the very carbonylation reactions (4) and (5).

The desired value of Re in the effluent from step (i) is attained by adjusting, for a given feed gas composition, the pressure and temperature in the reactor and possibly the space velocity. In Example 1 below this relation is 1.02 for the feed gas mixture in question ($H_2$ 33.4% vol., $H_2O$ 2.0% vol., CO 51.7% vol., $CO_2$ 11.8% vol.) and obtained by choosing a total pressure of 65 bar, a reaction temperature of 260° C. and a space velocity such that reactions (1) to (3) are close to equilibrium under these conditions, which will normally be the case. The value of Re=1.02 might also have been obtained by choosing other interdependent sets of pressure and temperature, e.g. 45 bar and 245° C. or 118 bar and 285° C. If a lower value of Re is desired, it is possible, under otherwise equal conditions, for example increase the reaction pressure or decrease the temperature or make a suitable combination of these measures; and conversely one may increase the value of Re under otherwise equal conditions by decreasing the pressure of the reaction or increasing the temperature or a combination thereof. This is due to the fact that the equilibria of reactions (1) to (3) depend in dissimilar way on the said parameters. Examples of interdependent values of pressure, temperature and the relation Re are shown in Table 1 below, in all cases the same feed gas composition having been used as in Example 1:

TABLE 1

| Feed gas mol % | | effluent, mol % | | | |
|---|---|---|---|---|---|
| | | 1 | 2 | 3 | 4 |
| | temp., °C. | 275 | 260 | 260 | 260 |
| | pressure, bar | 65 | 50 | 65 | 100 |
| 33.4 | $H_2$ | 11.9 | 11.1 | 8.5 | 5.2 |
| 2.0 | $H_2O$ | 0.2 | 0.2 | 0.2 | 0.1 |
| 51.7 | CO | 36.2 | 35.4 | 33.7 | 31.5 |
| 11.8 | $CO_2$ | 35.0 | 36.2 | 38.7 | 42.1 |
| 1.1 | $CH_4$ | 1.7 | 1.7 | 1.8 | 1.9 |
| | $CH_3OH$ | 1.3 | 1.1 | 1.1 | 1.1 |
| | $CH_3OCH_3$ | 13.6 | 14.3 | 15.9 | 18.1 |
| | Re | 1.27 | 1.20 | 1.02 | 0.84 |

In Example 2 there has been employed a feed gas and reaction conditions leading to a low value of Re, viz. Re=0.46.

As mentioned one may also increase the value of Re by increasing the space velocity because thereby one obtains a lower degree of conversion of synthesis gas into methanol and dimethyl ether and hence a larger amount of unreacted synthesis gas, including a higher amount of carbon monoxide.

As a catalyst for the carbonylation reactions in step (ii) there is particularly advantagelously employed a compound of a noble metal belonging to group VIII of the Periodic Table of Elements, combined with a promoter consisting of iodine, bromine or an organic or inorganic compound containing iodine and/or bromine. A known heterogenous catalyst is activated carbon impregnated with rhodium(III)chloride and an iodine compound such as methyl iodide.

The hydrolysis (8) of methyl acetate into acetic acid and methanol under the reaction conditions will normally assume equilibrium instantaneously because of the acidic medium and the pressure and temperature conditions employed.

The addition of water or steam between the first and the second reactor thus depends on whether acetic acid or methyl acetate/acetic anhydride is the preferentially desired product.

In case of acetic anhydride or methyl acetate being the desired main product, it is obvious that $H_2O$ should not be supplied between the two reactors. In that case it is moreover expedient to choose a catalyst which has no substantial activity with respect to the water gas reaction, and on the whole carry out the reaction in step (ii) under anhydrous or substantially anhydrous conditions, which, as appears from the Examples below, is easily obtained by a suitable choice of the composition of the feed gas, e.g. as stated in Example 1 and the above Table 1 in which the effluent from step (i) is approximately anhydrous because of the prevailing equilibrium conditions. In this connection it is to be observed that catalyst systems are known that do not catalyze the water gas shift reaction, as will be seen, a.o., of Examples below.

As mentioned one can choose the synthesis gas composition and the reaction conditions in the first reactor, step (i) such that the equilibrium of all of the three reactions is shifted far to the right hand side, whereby the relation Re defined hereinbefore will be lower that demanded by the stoichiometry of the desired acetic acid product. In that case it may be expedient according to the invention to have a catalyst catalyzing the water gas reaction (3) present in the reactor in which step (ii) is carried out. As mentioned, this will be the case when there is employed a rhodium catalyst in homogenous phase. The water gas reaction as mentioned is reversible, and the content of CO in the effluent from step (i) thereby is supplemented by virtue of $H_2$ and $CO_2$ from that effluent supplying the needful amount of Co for reactions (4) to (7) as CO is consumed in step (ii). In cases where the catalyst system in step (ii) has a significant activity for the water gas reaction, one thus may advantageously choose reaction conditions in step (i) in which the relation Re in the effluent from this step is lower than required in step (ii) for the full conversion of methanol and dimethyl ether. This deficit of carbon monoxide as explained above is set right via the water gas reaction in step (ii), providing from $H_2$ and $CO_2$ supplementing CO as CO is consumed in the carbonylation reactions (4) to (7). In this manner there may be obtained close to complete conversion of synthesis gas by solely one passage through the reactor system.

It is furthermore observed that a relation Re of about 1.0 in the effluent gas from step (i) may be advantageous when acetic acid or acetic anhydride is desired as the main product even if the amount of CO as described above may be adjusted by the water gas reaction in case of Re being below 1.0.

The process of the invention is to be described more fully in the following by the aid of the flow diagram shown in the Drawing.

In the drawing, 5 denotes a fresh synthesis gas which for instance originates from a conversion of natural gas or other hydrocarbons with steam and/or carbon dioxide, optionally supplemented with a recycle stream 9a which issues from a separator system 3 and is described more fully below. The synthesis gas may also originate from the gasification of coal or other raw materials. The synthesis gas 5 mainly contains hydrogen and carbon oxides.

The synthesis gas stream 5 may be passed directly in its entirety, without any wash, as a stream 5a,6 to a first reactor 1, or it may be passed as a stream 5b entirely or partly through a washing step 4 in which it is freed more or less from carbon dioxide, and from there further as a stream 6 to the first reactor 1.

In reactor 1, which is preferably a cooled reactor but may be adiabatic, the synthesis gas stream 6 is converted catalytically in gas phase into a mixture containing methanol and substantial amounts of dimethyl ether, most expediently at a pressure of 5-200 bar and a temperature of 150°-400° C. The entire effluent from reactor 1 is passed as a stream 7 to another reactor 2, optionally after having been mixed with first and second recycle streams 11 and 12, respectively, from separator system 3. If it is not the purpose to prepare pure acetic anhydride or pure methyl acetate, stream 7 may be further supplemented with a stream 13 of water or steam in such an amount that stream 7 passed to reactor 2 has a mol proportion $H_2O$/dimethyl ether between zero and about 1.

In reactor 2 methanol and dimethyl ether are carbonylated with carbon monoxide to form acetic acid, methyl acetate, acetic anhydride or mixtures thereof, and the effluent from reactor 2 is passed as a stream 8 to the separator system 3. Here the abovementioned streams, viz. a discharge stream 9 mainly consisting of hydrogen, carbon oxides and inert gases and being discharged from the system or optionally being used in its entirety or partly as a stream 9a as a source of heat or as a supplement to the feed synthesis gas 5 or for preparation thereof; a first recycle stream 11 mainly consisting of low boiling organic compounds, including dimethyl ether and possibly organic iodides such as methyl iodide, or bromides; a second recycle stream 12 mainly consisting of undesired carbonylation products and possibly water which may also contain one or more catalyst components, including organic and inorganic iodides; and at least one product stream of the desired acetic acid product, i.e. acetic acid, its methyl ester or its anhydride or a mixture of two or all three of these. If there is a net production of water in the overall reaction course, which may be the case when the water gas reaction (3) takes place in reactor 2, this water is discharged as a separate stream 14. At least some of the streams are cooled. Separation may for instance take place by distillation.

In the following the process according to the invention will be illustrated in further detail, firstly by three calculated Examples carried out in accordance with the above description of the flow diagram, secondly by three laboratory experiments in small scale. In the calculated Examples the content of catalyst components in the streams from reactor 2 have not been specified.

EXAMPLE 1

In this calculated Example, in which the compositions of the most important gas streams appear from Table 2 below, expressed as mol percent, there was employed a synthesis gas formed by reforming a gas containing $CO_2$ and $CH_4$ in the mol proportion 2:1 and $CH_4$ and $H_2$ in the mol proportion 0.1:1. In Table 2 the streams are numbered in accordance with the drawing.

A synthesis gas stream 5 of 5009 Nm$^3$/h is passed directly to reactor 1 in which a partial catalytic conversion into $CH_3OH$ and $CH_3OCH_3$ takes place at a pressure of 65 bar and a temperature of 260° C.

There is formed an effluent stream of 3018 Nm$^3$/h, which before the addition of 479 Nm$^3$/h steam 13 has the composition shown in Table 2 under heading 7 (Re=1.02); these two streams are passed together into reactor 2 in which conversion into the acetic acid product takes place at approximately the same pressure as in reactor 1 and at a temperature of 140° C.

The exit stream from reactor 2 is divided in separator system 3 into 995 Nm$^3$/h acetic acid 10 and a discharge or stream or recycle stream 9 (9a) of 1503 Nm$^3$/h.

TABLE 2

| Stream No. | 5 | 7 | 9 | 10 |
|---|---|---|---|---|
| Composition, mol % | | | | |
| $H_2$ | 33.4 | 8.5 | 17.0 | |
| $H_2O$ | 2.0 | 0.2 | | |
| CO | 51.7 | 33.7 | 1.5 | |
| $CO_2$ | 11.8 | 38.7 | 77.8 | |
| $CH_4$ | 1.1 | 1.8 | 3.6 | |
| $CH_3OH$ | | 1.1 | | |
| $CH_3OCH_3$ | | 15.9 | | |
| $CH_3COOH$ | | | | 100 |

EXAMPLE 2

This calculated Example illustrates the course when the carbonylation to form acetic acid in reactor 2 is combined with the water gas reaction. The most important in streams are shown in Table 3, expressed as the compositions in mol %. The numbers of the streams in Table 3 correspond to the drawing.

A synthesis gas stream 5 of 5848 Nm$^3$/h is led directly to the first reactor 1, where a partial catalytic conversion to form methanol and dimethyl ether is carried out at a pressure of 48 bar and a temperature of 270° C.

There is obtained an exit stream 7 of 3017 Nm$^3$ (Re=0.46), which is passed directly to the second reactor 2 in which methanol and dimethyl ether are converted to acetic acid at the same time as hydrogen and carbon monoxide are converted to steam and carbon monoxide at a pressure of about 48 bar and a temperature of 140° C.

There is formed a product stream 10 of acetic acid in an amount of 1402 Nm$^3$/h, a stream 14 of steam in an amount of 114 Nm$^3$/h and a discharge stream 9 in an amount of 99 Nm$^3$/h. Accordingly, practically all of the synthesis gas entered has been converted into acetic acid.

TABLE 3

| Stream No. | 5 | 7 | 9 | 10 |
|---|---|---|---|---|
| Composition, mol % | | | | |
| $H_2$ | 49.8 | 27.8 | 82.1 | |
| $H_2O$ | 1.9 | 0.6 | | |
| CO | 48.2 | 21.3 | | |
| $CO_2$ | | 25.1 | 0.4 | |
| $CH_4$ | 0.2 | 0.3 | 9.5 | |
| $CH_3OH$ | | 2.6 | 2.7 | |
| $CH_3OCH_3$ | | 22.1 | 5.3 | |
| $CH_3COOH$ | | | | 100 |

EXAMPLE 3

In this calculated Example the synthesis gas composition and the reaction conditions in reactor 1 have been selected such that methyl acetate becomes the end product. Moreover, the size and the composition of recycle streams have been specified.

Synthesis gas stream 6 is passed to reactor 1 in which it is converted catalytically to form methanol and dimethyl ether at a temperature of 257° C. and a pressure of 50 bar. The effluent 7 (Re=0.50) after the addition of recycle streams 11 and 12 is passed to reactor 2 in which methanol and dimethyl ether are carbonylated at a temperature of 250° C. and approximately the same pressure as in reactor 1. The effluent, which contains acetic acid and methyl acetate in equilibrium, are passed to separator system 3; from this a stream 9 or 9a is discharged, mainly containing hydrogen, methane and carbon dioxide, as well as a stream of water 14, a product stream 10 of methyl acetate and the abovementioned recycle streams 11 and 12.

TABLE 4

| Stream No. | 6 | 7 | 8 | 9 | 10 | 11 | 12 | 14 |
|---|---|---|---|---|---|---|---|---|
| Flow (Nm$^3$/h) | 18250 | 9434 | 8300 | 4910 | 2200 | 290 | 778 | 113 |
| Composition, mol-% | | | | | | | | |
| $H_2$ | 44.2 | 16.2 | 18.4 | 31.1 | | | | |
| $H_2O$ | 1.0 | 0.3 | 1.4 | | | | | 100 |
| CO | 48.7 | 23.4 | | | | | | |
| $CO_2$ | 1.9 | 27.8 | 31.6 | 53.4 | | | | |
| $CH_4$ | 4.2 | 8.1 | 9.2 | 15.5 | | | | |
| $CH_3OH$ | | 1.8 | 0.5 | | | | 5.1 | |
| $CH_3OCH_3$ | | 22.5 | 3.5 | | | 100 | | |
| $CH_3COOH$ | | | 8.9 | | | | 94.8 | |
| $CH_3COOCH_3$ | | | 26.6 | | 100 | | | |

EXAMPLE 4

5.00 g of a catalyst pelletized as one lot and consisting of 90% by weight (w) of a mixture of CuO, ZnO and $Al_2O_3$ and containing Cu, Zn and Al in the mol ratio 60:25:15, as well as 10% w of zeolite HZSM-5 with a Si/Al ratio of 35 were placed in a reactor and activated by heating in a gas stream (flow velocity about 4 Nl/h) containing about 2% by volume (v) of hydrogen in nitrogen, at atmospheric pressure and a temperature increasing from ambient temperature to 250° C. at a rate of 0.04° C./minute. In another reactor there was placed at beforehand 2.50 g of a carbonylation catalyst containing about 0.5% (w) of rhodium, prepared by the impregnation of activated carbon with an aqueous solution of rhodium (III) chloride. This catalyst was activated at 120° C. and atmospheric pressure simultaneously with the catalyst in the first reactor, the exit gas from the first reactor being used as activation gas for the rhodium catalyst. When the temperature in the first reactor had reached 250° C., the input into it was changed to a feed gas composed so as to simulate a feed gas formed in known manner by reforming natural gas with $CO_2$, and consisting of (percent by volume): $H_2$ 36.2%, CO 47.1% and $CO_2$ 13.0%. Moreover, the gas contained 3.62% Ar which served as internal standard. This gas thereafter passed through both of the two reactors in series at a rate, measured at the entrance to reactor 1, of about 4 Nl/h. Now the temperature in reactor 2 was increased to 180° C. and the reactor was put under a pressure of 51 bar, after which the gas velocity into reactor 1 was increased to 19 Nl/h. The connection between the two reactors was kept hot (250° C.) in order to avoid a possible condensation of reaction products. Now methyl iodide was admitted in an amount of 0.53 g/h into the product stream from reactor 2 in order to partly simulate the recycle stream 11 shown in the drawing.

Characteristics of the inlet and exit streams to and from the two reactors are shown in table 5 below:

TABLE 5

| | Inlet, 1st reactor | Exit, 1st reactor | Inlet, 2nd reactor | Exit, 2nd reactor |
|---|---|---|---|---|
| Pressure (bar) | 51 | 51 | 51 | 51 |
| Temperature (°C.) | 250 | 250 | 180 | 180 |
| Gas velocity (Nl/h) | 19.03 | 12.71 | (12.80) | 11.55 |
| Component stream (mmol/hr.) | | | | |
| Ar | 30.7 | (30.7) | (30.7) | (30.7) |
| $H_2$ | 307 | 71.5 | 71.4 | 70.6 |
| $H_2O$ | | | | 0.17 |
| CO | 400 | 204 | 204 | 157 |
| $CO_2$ | 110 | 177 | 177 | 176 |
| $CH_4$ | | | | |
| $CH_3OH$ | | 13.0 | 13.0 | 1.8 |
| $CH_3OCH_3$ | | 69.2 | 69.2 | 33.3 |
| $CH_3I$ | | | 3.74 | 3.62 |
| $CH_3CO_2H$ | | | | 9.8 |
| $CH_3CO_2CH_3$ | | | | 37.0 |
| $(CH_3CO)_2O$ | | | | 1.75 |

It is calculated that Re in this experiment assumes the value 1.34. It is observed by inspection of the streams into and out of reactor 2 that it is not adjusted to equilibrium for the water gas reaction and that no demonstrable alterations of the absolute amounts of hydrogen and carbon dioxide have taken place during the passage of the gas through the second reactor.

EXAMPLE 5

This experiment has been carried out in a similar manner as Example 4, but differs therefrom thereby that not only methyl iodide but also steam was added to the product stream from the first reactor. Characteristics of the streams into and out of the two reactors are contained in Table 6 below.

TABLE 6

| | Inlet, 1st reactor | Exit, 1st reactor | Inlet, 2nd reactor | Exit, 2nd reactor |
|---|---|---|---|---|
| Pressure (bar) | 51 | 51 | 51 | 51 |
| Temperature (°C.) | 250 | 250 | 180 | 180 |
| Gas velocity (Nl/h) | 30.54 | 22.4 | (23.18) | 21.87 |
| Component stream (mmol/hr.) | | | | |
| Ar | 48.0 | (48.0) | (48.0) | (48.0) |
| $H_2$ | 486 | 181 | 181 | 181 |
| $H_2O$ | | | 32.8 | 27.0 |
| CO | 658 | 415 | 414 | 375 |

TABLE 6-continued

|  | Inlet, 1st reactor | Exit, 1st reactor | Inlet, 2nd reactor | Exit, 2nd reactor |
|---|---|---|---|---|
| $CO_2$ | 169 | 249 | 249 | 247 |
| $CH_4$ |  |  |  |  |
| $CH_3OH$ |  | 26 | 26 | 10.8 |
| $CH_3OCH_3$ |  | 80.1 | 80.1 | 57.6 |
| $CH_3I$ |  |  | 3.31 | 3.25 |
| $CH_3CO_2H$ |  |  |  | 12.3 |
| $CH_3CO_2CH_3$ |  |  |  | 27.2 |
| $(CH_3CO)_2O$ |  |  |  | 0.0 |

It is seen from Table 6 how the higher space velocity in this Example, compared to Example 4, causes an increased value of the relation Re in the product stream from the first reactor. As in Example 4 it is observed that the catalyst does not exert demonstrable activity for the water gas reaction.

EXAMPLE 6

This experiment has been conducted in a similar manner as that described in Example 4, but differs from it in considerably lower space velocities and a slightly higher reaction pressure, 60 bar; and furthermore the composition of the synthesis gas has been altered to (percent by volume): $H_2$ 35.1%, CO 47.6%, $CO_2$ 13.0% and Ar 4.34% (as internal standard). In the second reactor the amount of rhodium catalyst has been increased to 3.00 g. The characteristics of the streams to and from the two reactors are shown in Table 7 (note that Re in this Example assumes the value of 1.07):

TABLE 7

|  | Inlet, 1st reactor | Exit, 1st reactor | Inlet, 2nd reactor | Exit, 2nd reactor |
|---|---|---|---|---|
| Pressure (bar) | 60 | 60 | 60 | 60 |
| Temperature (°C.) | 250 | 250 | 180 | 180 |
| Gas velocity (Nl/h) | 7.00 | 4.38 | (4.44) | 4.03 |
| Component stream (mmol/hr.) |  |  |  |  |
| Ar | 13.6 | (13.6) | (13.6) | (13.6) |
| $H_2$ | 110.0 | 14.8 | 14.8 | 14.6 |
| $H_2O$ |  |  |  |  |
| CO | 149.1 | 69.8 | 69.8 | 53.9 |
| $CO_2$ | 40.8 | 64.0 | 64.0 | 64.2 |
| $CH_4$ |  |  |  |  |
| $CH_3OH$ |  | 1.8 | 1.8 | 1.1 |
| $CH_3OCH_3$ |  | 31.6 | 31.6 | 15.0 |
| $CH_3I$ |  |  | 2.88 | 2.98 |
| $CH_3CO_2H$ |  |  |  | 0.5 |
| $CH_3CO_2CH_3$ |  |  |  | 15.7 |
| $(CH_3CO)_2O$ |  |  |  | 0.2 |

From column 2 of the Table it is calculated that Re = 1.07. As in the foregoing Examples no water gas activity of the carbonylation catalyst has been observed.

We claim:

1. A process for preparing an acetic acid product selected from the group consisting of acetic acid, methyl acetate, acetic anhydride and mixtures thereof by conversion of a synthesis gas mainly consisting of hydrogen and carbon oxides, said process comprising the steps of:
   (i) introducing said synthesis gas into a first reactor at a pressure of 5-200 bar and a temperature of 150°-400° C., and converting said synthesis gas therein in the gas phase into methanol and dimethyl ether in the presence of a catalyst selected from the group consisting of a mixture of $CuO-ZnO-Al_2O_3$ having a composition of about 60 atom % Cu, 25 atom % Zn and 15 atom % Al, and a zeolite so as to obtain a mol proportion 0.1:1 to 3:1 of carbon monoxide to methanol plus dimethyl ether, said mol proportion being defined by the expression $CO/(CH_3OH+2CH_3OCH_3)$, and then
   (ii) carbonylating the mixture formed in step (i) by passing the effluent from the first reactor to a second reactor and converting methanol and dimethyl ether therein in a fluid phase to said acetic acid product at a pressure of 1-800 bar and a temperature of 100°-500° C. in the presence of a catalyst consisting of activated carbon impregnated with rhodium(III)chloride and methyl iodide and then
   (iii) recovering from effluent of said second reactor at least one product stream consisting of the acetic acid products.

2. The process according to claim 1, wherein the conversion in step (ii) is carried out at substantially the same pressure as in step (i).

3. The process according to claim 1, further comprising the step of adding $H_2O$ to the effluent of the first reactor in an amount such that the effluent of the first reactor has a mol proportion of $H_2O$ to dimethyl ether of up to 10.

4. The process according to claim 1, wherein said synthesis gas is converted in said first reactor so as to obtain a mol proportion of carbon dioxide to methanol plus dimethyl ether in the effluent from said first reactor which is an optimal mol proportion for the acetic acid product or products.

5. The process according to claim 4, wherein said synthesis gas is converted in said first reactor so that a mol proportion of carbon monoxide to methanol plus dimethyl ether of approximately 1 is maintained in the first reactor and acetic acid and/or acetic anhydride is predominantly formed by the process.

6. The process according to claim 4, wherein said synthesis gas is converted in said first reactor so that a mol proportion of carbon monoxide to methanol plus dimethyl ether of approximately 0.5 is maintained in the first reactor and methyl acetate is predominantly formed by the process.

* * * * *